US011664095B2

(12) United States Patent
Rudolph

(10) Patent No.: US 11,664,095 B2
(45) Date of Patent: *May 30, 2023

(54) MAVIN ANALYSIS AND REPORTING SYSTEMS AND METHODS FOR SCALING AND RESPONSE INSIGHTS IN SURVEY RESEARCH

(71) Applicant: Laurence Rudolph, Herndon, VA (US)

(72) Inventor: Laurence Rudolph, Herndon, VA (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/195,793

(22) Filed: Mar. 9, 2021

(65) Prior Publication Data
US 2021/0265026 A1 Aug. 26, 2021

Related U.S. Application Data

(63) Continuation of application No. 17/023,527, filed on Sep. 17, 2020, now Pat. No. 10,978,182.

(60) Provisional application No. 62/901,395, filed on Sep. 17, 2019.

(51) Int. Cl.
*G16H 10/20* (2018.01)
*G16H 50/30* (2018.01)

(52) U.S. Cl.
CPC ............ *G16H 10/20* (2018.01); *G16H 50/30* (2018.01)

(58) Field of Classification Search
CPC ................................ G16H 10/20; G16H 50/30
USPC ........................................................ 705/2–3
See application file for complete search history.

(56) References Cited

U.S. PATENT DOCUMENTS

| 8,540,514 B2 * | 9/2013 | Gosling | G09B 7/00 |
| | | | 455/2.01 |
| 2002/0052774 A1 * | 5/2002 | Parker | G06Q 30/02 |
| | | | 705/7.32 |
| 2007/0192163 A1 * | 8/2007 | Barr | G06Q 30/0203 |
| | | | 705/7.32 |
| 2015/0310462 A1 * | 10/2015 | Garcia | G06Q 30/0203 |
| | | | 705/7.32 |

(Continued)

OTHER PUBLICATIONS

Wikipedia, Aug. 23, 2019, Likert Scale—https://web.archive.org/web/20190823163955/https://en.wikipedia.org/wiki/Likert_scale (Year: 2019).*

(Continued)

*Primary Examiner* — Joy Chng
(74) *Attorney, Agent, or Firm* — Raphael Bellum PLLC

(57) ABSTRACT

The Mavin systems and computer-implemented processes of the invention analyze, score, and report the results from Likert scale survey questions. The systems and methods address three weaknesses in traditional Likert scale analyses by providing: (1) a scoring procedure that is sensitive to all levels of response; (2) a determination and designation of a standard score used to determine whether the results meet that standard; and (3) a scoring process used to determine the degree to which a given score exceeds or fails to meet this standard. In addition, the Mavin systems and methods support recalculation and adjustment to the scoring model when available data support such adjustments. Further, the Mavin systems and methods incorporate flexible non-linear segment intervals and determine evidence-based adjusted response segment values to determine adjusted Mavin scores and provide actionable survey results.

20 Claims, 5 Drawing Sheets

(56) References Cited

U.S. PATENT DOCUMENTS

2016/0027129 A1* 1/2016 Pallaghy ................ G06Q 50/01
                                                        705/319
2018/0225602 A1* 8/2018 Joi ........................ G06T 11/206

OTHER PUBLICATIONS

Avila et al., Oct. 28, 2015, A Critical Review of Scoring Options for Clinical Measurements Tools, BMC Research Notes 8, 612 (2015), https://doi.org/10.1186/s13104-015-1561-6 (Year: 2015).*
Wikipedia, Likert Scale, Aug. 23, 2019, https://web.archive.org/web/20190823163955/https://en.wikipedia.org/wiki/Likert_scale (Year: 2019).
Avila et al., A Critical Review of Scoring Options for Clinical Measurements Tools, Oct. 28, 2015, BMC Research Notes 8, 612 (2015), https://doi.org/10.1186/s 13104-015-1561-6 (Year: 2015).

* cited by examiner

MAVIN ANALYSIS AND REPORTING SYSTEMS AND METHODS FOR SCALING AND RESPONSE INSIGHTS IN SURVEY RESEARCH

CROSS-REFERENCES TO RELATED APPLICATIONS

This application is a continuation of U.S. application Ser. No. 17/023,527 filed on Sep. 17, 2020, which claims benefit of priority to U.S. provisional application No. 62/901,395 filed on Sep. 17, 2019. All applications and documents cited in this application are incorporated by reference in their entireties in this application.

TECHNICAL FIELD

This technology relates to computerized evaluation systems and methods for analyzing aggregate survey research data and providing actionable intelligence based on the analysis.

BACKGROUND

Surveys are used as a means of data collection for understanding customers, markets, products, and services. Surveys bridge businesses and customers and can be used to gauge customer perception of quality, value, and performance. To extract value from a survey, the survey responses need to be efficiently and accurately captured and analyzed. Data visualization models can allow inspection of the survey data to identify relationships within survey data, to identify patterns in responses, and to draw conclusions regarding the business and/or its customers. However, the usefulness of the survey data cannot be properly leveraged if the visualization models are time-consuming, hard to understand, limited in interaction, or unable to explore interrelationships within the survey data.

Likert scales are a common ratings format for surveys and include a bipolar response (e.g., positive and negative about a neutral, middle option) with scale ranges of the responses from a group of anchored categories, such as least to most, agree or disagree, approve or disapprove, and believe to be true or false. Respondents rank their level of response from high to low or from best to worst using a discrete number of anchored levels, such as five or seven levels. One possible Ukert scale may include five discrete and symmetric responses (levels) that include Strongly Disagree, Disagree, Neutral, Agree, and Strongly Agree. Similar Likert scale ranges are used in other categories of responses. Survey research studies frequently use Likert scales as the format for opinion questions. Likert-scale questions give respondents a range of options—for example, starting at "not at all likely," scaling all the way up to "extremely likely" to measure respondent opinions or attitudes. Likert scales attempt to capture the intensity of respondents' feelings for a given item.

Likert scales have been used to measure character and personality traits as well and have implemented a series of questions with discrete levels of response alternatives (e.g., Strongly Approve, Approve, Undecided, Disapprove, and Strongly Disapprove, for example, as well as the other examples above). Analysis of these responses is based on a composite score from the series of questions that represent the attitudinal scale. Past analyses of responses have included errors attributed to differences in Likert-type items and Likert scales. Likert-type items are single questions that use an aspect of original Likert response alternatives. Multiple questions can be used in a research survey, but no attempt is made to combine the responses into a composite scale. A Likert scale, in contrast, includes a series of four (or more) Likert-type items that are combined into a single composite score when analyzed. When combined, the items can be used to provide a quantitative measure of the studied quality.

Statisticians have generally grouped data collected from surveys into a hierarchy of measurement levels, including nominal data, ordinal data, interval data, and ratio data. Nominal data include observations that are assigned to categories based on equivalence. Nominal data are often regarded as the weakest level of measurement representing categories without numerical representation. Numerical values associated with the nominal data categories serve only as labels. Examples of nominal scale data include gender, eye color, and race.

Ordinal scale responses include a ranking or ordering of responses using some measure of magnitude. Numbers (or letters) assigned to groups express a relative relationship (e.g., "greater than" or "lesser than"), but there is no measure of how much greater or lesser. The numbers or letters indicate only the order, but no measure of greater or lesser distance is possible. Examples of ordinal scale measures include letter grades, rankings, and achievement (low, medium, high). Interval scale data use integers to indicate order and to reflect a relative distance between points on the scale. Also, interval scales do not have an absolute zero. One example of an interval scale is an IQ standardized test. A ratio scale also uses numbers to indicate order and distance between points on the scale and can use fractional values between variables. A ratio scale does have an absolute zero. Ratio measure examples include age and years of experience.

Data analyses using nominal, interval, and ratio data are accepted as generally clear and understandable. Ordinal data analysis, including analysis of Likert (and other) scales in surveys, is not as straightforward. The adequacy of treating ordinal data as interval data continues to be controversial in survey analyses in a variety of applied fields. Whether individual Likert items can be considered as interval-level data or whether they should be treated as ordered-categorical data is the subject of considerable disagreement.

Scale numbers (i.e., segment values) assigned to Likert-type items express a "greater than" relationship, but "how much" greater is not implied. Therefore, Likert-type items are ordinal measures. Descriptive statistics recommended for ordinal measurement scale items include a mode or median for central tendency and frequencies for variability. Other analysis procedures appropriate for ordinal scale items include the chi-square measure of association (contingency), which is a measure of the significance of association between two categorical variables rather than a measure of the strength of the association.

Likert scales are arbitrary. The segment value assigned to a Likert item has no objective numerical basis, either in terms of measure theory or scale (from which a distance metric can be determined). The segment value assigned to each Likert item is determined by the researcher designing the survey, who makes the decision based on a desired level of detail. By convention, Likert items tend to be assigned progressive positive integer values. Likert scales typically range from 2 to 10 items—with 3 or 5 items being the most common. The progressive structure of the scale provides that each successive Likert item is treated as indicating a "better"

response (i.e., more positive) than the preceding segment value (unless reverse ordering of the Likert Scale is used).

The "distance" between each successive item category in traditional Likert scales is equivalent. For example, in a Five-Option Likert scale, the inference is that the "distance" between response category 1 and response category 2 is the same as between response category 3 and response category 4. An equidistant presentation by the survey designer and researcher is important to help avoid bias in analyzing the results of a survey. For example, a Five-Option Likert scale with categories "Poor," "Average," "Good," "Very Good," and "Exceptional" does not have equidistant response categories because there is only one response category that can receive a below-average rating. This would likely bias any result in favor of a positive outcome. However, even if a study designer or researcher presents what they believe are equidistant categories, they may not be interpreted as such by the respondents.

As above, a properly constructed Likert scale presents symmetrical response categories about a neutral midpoint, with clearly defined linguistic qualifiers. With symmetric scaling, equidistant attributes will be more clearly observed or inferred. When a Likert scale is symmetric and equidistant, it behaves more like an interval-level measurement. While a Likert scale is ordinal, if well designed and presented, it can approximate an interval-level measurement, which can be beneficial because some valuable information can be lost if the "distance" between Likert items was not available for consideration. However, problems exist when analyzing Likert items as an interval measurement without regard for the linearity and symmetry of the scale responses (i.e., as opposed to categories). No accommodation is typically given for custom analysis of survey responses where the scale responses are found to be non-linear and/or asymmetrical.

Other problems exist with conventional analysis of Likert scale results. Traditional methods of analyzing the results from surveys using Likert scales may provide valid results, but they fail to fully address three critical factors.

First, each of the anchored response options must be differentiated from the others when calculating the results. Combining two or more of the responses into a single category limits the power of the analysis. For example, it is common practice to combine the responses of Very Satisfied and Satisfied into a single category called "Combined Percent Satisfied" (CPS). This combination action greatly simplifies the interpretation of the data, but in doing so, it ignores the difference between a satisfied customer and a very satisfied one. "Except in a few rare instances, complete customer satisfaction is the key to securing customer loyalty and generating superior long-term financial performance. Most managers realize that the more competitive the market, the more important the level of customer satisfaction. What most do not realize, however, is just how important the level of customer satisfaction is in markets where competition is intense, such as hard and soft durables, business equipment, financial services, and retailing. In markets such as these, there is a tremendous difference between the loyalty of merely satisfied and completely satisfied customers." See Jones, Thomas O. and W. Earl Sasser, Jr., "Why Satisfied Customers Defect," Harvard Business Review, November-December 1995.

Second, there must be a valid, easily interpretable, method for discerning the degree of difference, or lack thereof, between, amongst, and within respondents or groups of respondents. CPS lacks a defensible way to interpret the degree to which results from two or more surveys differ. This capability is needed to make valid comparisons of the results from different individuals or groups of individuals, or to measure changes over time.

Another example of current analysis inadequacies is shown in Table 1 below, where the first set of results (Set 1) measures a CPS of 90% and would be considered inferior to the second set of results (Set 2) which measures a CPS of 92%. Very few decision makers carefully reviewing these data would agree with this conclusion. CPS, by ignoring the difference between Satisfied and Very Satisfied, lacks a credible way to support such decisions.

TABLE 1

|  | Very Satisfied | Satisfied | Neutral | Dissatisfied | Very Dissatisfied | Combined Percent Satisfied (CPS) |
| --- | --- | --- | --- | --- | --- | --- |
| Set 1 | 80 | 10 | 7 | 3 | 0 | 90% |
| Set 2 | 15 | 77 | 4 | 2 | 2 | 92% |

Third, there needs to be a defensible standard (benchmark) for judging the performance of individuals, as well as for making valid comparisons between, amongst, and within different respondents or groups of respondents. CPS lacks the ability to set a defensible standard. For example, two sets of responses are displayed in Table 2 below.

TABLE 2

|  | Very Satisfied | Satisfied | Neutral | Dissatisfied | Very Dissatisfied | Combined Percent Satisfied (CPS) |
| --- | --- | --- | --- | --- | --- | --- |
| Set 3 | 60 | 29 | 7 | 4 | 0 | 89% |
| Set 4 | 15 | 75 | 4 | 4 | 2 | 90% |

Clearly these two sets of results are not equivalent. If the standard for evaluating these results were to be set at 90%, the second set of results (Set 4, CPS=90%) would be deemed acceptable, whereas the first set of results (Set 3, CPS=89%) would be deemed not acceptable. Very few decision makers closely reviewing these data sets would agree. The same could be said for any such value based on "Combined Percent Satisfied."

These technological problems create limitations to a user's ability to analyze and understand nuanced results, and past attempts to create technical solutions have been unsuccessful and unreliable. These difficulties in measuring attitudes, character, personality traits and other respondent impressions lies in the lack of processes and procedures for transferring these qualities into a quantitative measure for data analysis and visualization purposes that can address shortcomings of conventional systems.

SUMMARY

The systems and methods in accordance with the invention (Mavin) provide an elegant solution to problems of prior systems in reviewing, analyzing, communicating, and displaying respondent impressions from survey data. The systems and methods of the invention identify, categorize, and classify study results and transfer these qualities into quantitative measures for data analysis and visualization purposes that tackle the inadequacies of prior efforts.

Systems and methods of the invention analyze results from psychometric instruments and determine a Mavin Score in real time, and provide immediate reporting services and solutions based on the Mavin Score. The dynamic credit limit systems and methods described in this disclosure provide a technological solution to an issue rooted in technology, including improved systems and methods for processing and analyzing disparate data in large volumes at scale from multiple sources.

The Mavin systems and methods analyze results from questions using fully anchored Likert scales, where each response category is linked to a unique descriptor. For example, a fully anchored Likert scale measuring customer satisfaction includes the following descriptors: Very Dissatisfied, Dissatisfied, Neutral, Satisfied, and Very Satisfied. There are also fully anchored Likert scales with three descriptor options (Dissatisfied, Neutral, and Satisfied), four descriptor options (Very Dissatisfied, Dissatisfied, Satisfied, and Very Satisfied), six descriptor options (Very Dissatisfied, Dissatisfied, Somewhat Dissatisfied, Somewhat Satisfied, Satisfied, Very Satisfied), and seven descriptor options (Very Dissatisfied, Dissatisfied, Neutral, Somewhat Dissatisfied, Somewhat Satisfied, Satisfied, Very Satisfied). The Mavin systems and methods of the invention can be applied to any of these fully anchored Likert scale versions. There are also 10- and 11-option Likert scales (using, respectively, 1 to 10 and 0 to 10), but they are not fully anchored, and are not addressed in the examples below.

For clarity and consistency, this disclosure describes exemplary implementations of Mavin systems and methods using the Five-Option satisfaction scale described above-Very Dissatisfied, Dissatisfied, Neutral, Satisfied, and Very Satisfied. Other Likert scales, including a Seven-Option fully anchored agreement scale, can use similar methods but include adjustments to incorporate the two additional options.

The Mavin survey analysis and reporting systems address problems and issues described above. Namely, the Mavin survey analysis and reporting systems provides an optimal analysis and reporting system by: 1) scoring the survey results using a different segment value for each of the anchored options; 2) generating valid, reliable, easily interpretable results, capable of discerning the degree of difference between the scores from two or more individuals or groups taking a survey; and 3) supporting the designation of a defensible standard (i.e., benchmark) for judging results using the above score.

Supporting the first critical factor, in one exemplary implementation of the Mavin invention, the system and process assigns segment values 1.00 through 5.00 to the five response options: Very Dissatisfied (1.00), Dissatisfied (2.00), Neutral (3.00), Satisfied (4.00), and Very Satisfied (5.00). The Mavin processes determine the mean value of all responses to obtain a Mavin Score. The Mavin systems and methods address problems with prior systems discussed above related to differentiating the anchored response options by treating each of the five options individually. The Mavin systems and methods do not combine any of the five response categories.

The Mavin systems and methods address the second important issue by applying a characteristic of the mean value. That is, the analysis performed by the exemplary implementations of Mavin systems in accordance with the invention uses the mean rather than the percentage to compare two or more data sets constructed from Five-Option Likert scales. As noted above (see Table 1), the Combined Percent Satisfied (CPS) measure lacks the ability to make valid, consistent comparisons of Five-Option Likert scale data sets. This is due in part to the CPS combining responses across the two levels of satisfaction (e.g., Very Satisfied and Satisfied), and the three levels that are less than satisfied (e.g., Neutral, Dissatisfied, and Very Dissatisfied). The Mavin systems and methods use the mean as the comparator to provide valid, easily interpretable results that support a method for discerning the relative difference between two or more survey deliveries.

Surveys using Likert scales are psychometric instruments designed to measure respondents' preferences, opinions, beliefs, level of satisfaction, etc. An exemplary implementation of the invention includes a computerized evaluation system for storing, scoring, and reporting (survey) results. The (Mavin) systems include a processor for executing applications stored in a non-transitory computer-readable medium of a computer. The applications include a receiving application, a scoring application, and a reporting application.

The receiving applications are configured to receive study results and store them in a survey database. The study results can be received directly from respondents or from an evaluations server or other party/device that provides the evaluations. The study data can include responses to questionnaires, interviews, evaluation forms, surveys, and other study data. In some embodiments of the invention, the psychometric study results include Likert scales for satisfaction, importance, confidence, and agreement, among others. The Likert scales can be fully anchored, and a predetermined number of segments can be five or seven, for example.

The scoring applications are configured to compute and determine a Mavin Score from the stored study results, where the Mavin Score determination includes segmenting the study results to reflect the fully anchored scale with the predetermined number of segments. In one exemplary implementation of the invention a Five-Option Likert scale is used.

Determining the Mavin Score also includes weighting each of the segments with a segment score. The segment value (score) is the value that is assigned to that particular segment of the scale. For example, in a Five-Option Likert scale, the values of 5, 4, 3, 2, and 1 are the respective segments of the fully anchored scale. In a Five-Option Likert scale, 1 is assigned to Very Dissatisfied, 2 is assigned to Dissatisfied, 3 is assigned to Neutral, 4 is assigned to Satisfied, and 5 is assigned to Very Satisfied.

The Mavin systems continue with determinations of Mavin Scores by determining and setting a defensible standard score based on the number of predetermined segments. The defensible standard score will vary based on the number of predetermined segments and the segment value assigned to each of the segments. For Five-Option Likert scales, a defensible standard can have one value, but for Likert scales with other numbers of options, the defensible standard score can have a different value. One example implementation of the invention uses "Satisfactory" as the defensible standard and the segment score of 4.00, which corresponds to "Satisfactory" on many Five-Option Likert scales.

The Mavin processes continue in determining the Mavin Scores by assigning a value to each segment of the study results. The extracted interval scoring data include a predetermined interval weighting. In most cases, the Likert scales are symmetrical, and the default segment value weighting for the extracted interval scoring data is 1.00. The symmetry of the Likert scales used in the Mavin processes (e.g., balanced syntax in constructing the labels for the segments, equal spacing of response options on the survey forms, and the inclusion of value labels for each of the segments) reinforces the perception of linearity of the scaling. However, when there is evidence that the true measure of the scale is non-linear, the Mavin processes include tools and mechanisms to make adjustments to the interval weighting.

For example, where evidence includes findings that customers who are Very Dissatisfied are far more likely to stop doing business than customers who are Dissatisfied, the system can adjust the weighting for the Very Dissatisfied segment that results in a score of 0.75 rather than 1.00. Similarly, where evidence includes findings that customers who are Neutral are only slightly less likely to take a positive action than customers who are Satisfied, the system can raise the weighting for the Neutral segment score to 3.25 rather than 3.0.

The systems and methods of the invention then generate a Mavin Score based on the number of segments, the segment values, and the interval scoring data. In one example implementation of the invention, the Mavin Score is the total of the products of the individual segment values and the number of responses for that segment, all of which are divided by the total number of responses. The invention then automatically compares the computed Mavin Score to the defensible standard score and interprets the results. In some example implementations of the invention, the interpretation incorporates a (single) weighted evaluation of the scores. The Mavin Score is comprised of two parts: the integer part, which is the number to the left of the decimal, and the fractional part, which are the numbers to the right of the decimal. The integer part equates to the outcome segment that best describes the general results of the study. The fractional part is the weighted percent of the respondents representing that segment.

Some exemplary implementations of the invention include the fully anchored Likert scale with five predetermined segments. In these embodiments, when the Mavin Score is greater than 4.00, the integer portion of the single weighted evaluation metric has a segment value of "4," then the respondents' general characterization is classified as Very Satisfied, and the fractional part of the single weighted evaluation metric designates the weighted percent of Very Satisfied respondents. So, a value of 4.27 would indicate that the surveyed population trends toward Very Satisfied, and the fractional part would answer the question, "To what degree is the surveyed population very satisfied?" In this case, the answer would be 27%.

When the integer part of the single weighted evaluation metric has a value greater than 3.00 but less than 4.00, then the respondents' general characterization of the study results is classified as Satisfied, and the fractional part of the single weighted evaluation metric designates the weighted percent of Satisfied respondents. A Mavin Score of 3.65 would be characterized as Satisfied, and that 65% of the respondents would be the weighted percent that were satisfied.

When the integer part of the single weighted evaluation metric has a value greater than 2.00 but less than 3.00, the respondents' general characterization of the study results is classified as Neutral, and the fractional part of the single weighted evaluation metric designates the weighted percent of Neutral respondents. A Mavin Score of 2.85 would be characterized as Neutral, and that 85% of the respondents would be the weighted percent that were neutral.

When the integer part of the single weighted evaluation metric has a value greater than 1.00 but less than 2.00, then the respondents' general characterization of the study results is classified as Dissatisfied, and the fractional part of the single weighted evaluation metric designates the weighted percent of Dissatisfied respondents. A Mavin Score of 1.48 would be characterized as Dissatisfied, and that 48% of the respondents would be the weighted percent that were dissatisfied.

When the integer part of the single weighted evaluation metric has a value equal to 1.00, then the respondents' general characterization of the study results is classified as Very Dissatisfied, and the fractional part of the single weighted evaluation metric must be 100% Very Dissatisfied since there is no response less than 1.

In some exemplary implementations of the invention, the single weighted evaluation metric generated by the reporting application is compared to a single weighted evaluation metric of a different entity (e.g., organization, group, individual, etc.) as a measure of the relative performance of these entities.

In some exemplary implementations of the invention, one or more prior evaluation metrics are compared to an additional evaluation metric for the entity to track relative performance of the entity over time.

In some exemplary implementations of the invention, the single weighted evaluation metric generated by the reporting application is compared to a series of additional single weighted evaluation metrics for the entity to determine the degree to which the entity exceeds or falls short of the defensible standard score.

In some exemplary implementations of the invention, the single weighted evaluation metric is compared to additional single weighted evaluation metrics of other entities to compare the relative performance of the entities. For example, the single weighted evaluation metric generated by the reporting application for the entity is compared to a metric value for each of two (or more) other entities to measure the degree to which the entity surpasses or lags behind the other entities.

In some exemplary implementations of the invention, the single weighted evaluation metric generated by the reporting application is compared to a series of additional single weighted evaluation metrics for the entity to determine the degree to which an entity's performance increases or decreases over time.

The systems and methods of the invention include a reporting application that sends the evaluation metric and the comparisons and performance characterizations to a display device of a user.

The reporting application can provide a real-time, customizable graphical user interface to the display device of the user and display the psychometric study results by segments in the fully anchored scale as well as display the determined Mavin Score of the psychometric study results. The reporting application can be customized by the user to display an ordered set of psychometric study results based on the Mavin Score. Comparisons can be made using the reporting application that include comparisons of respondents, entities, survey responses, and other variables (additional responses, for example). The comparisons can be customized and displayed as charts, graphs, infographics, diagrams, maps, and other data visualization presentations.

DETAILED DESCRIPTION

Figure 1:
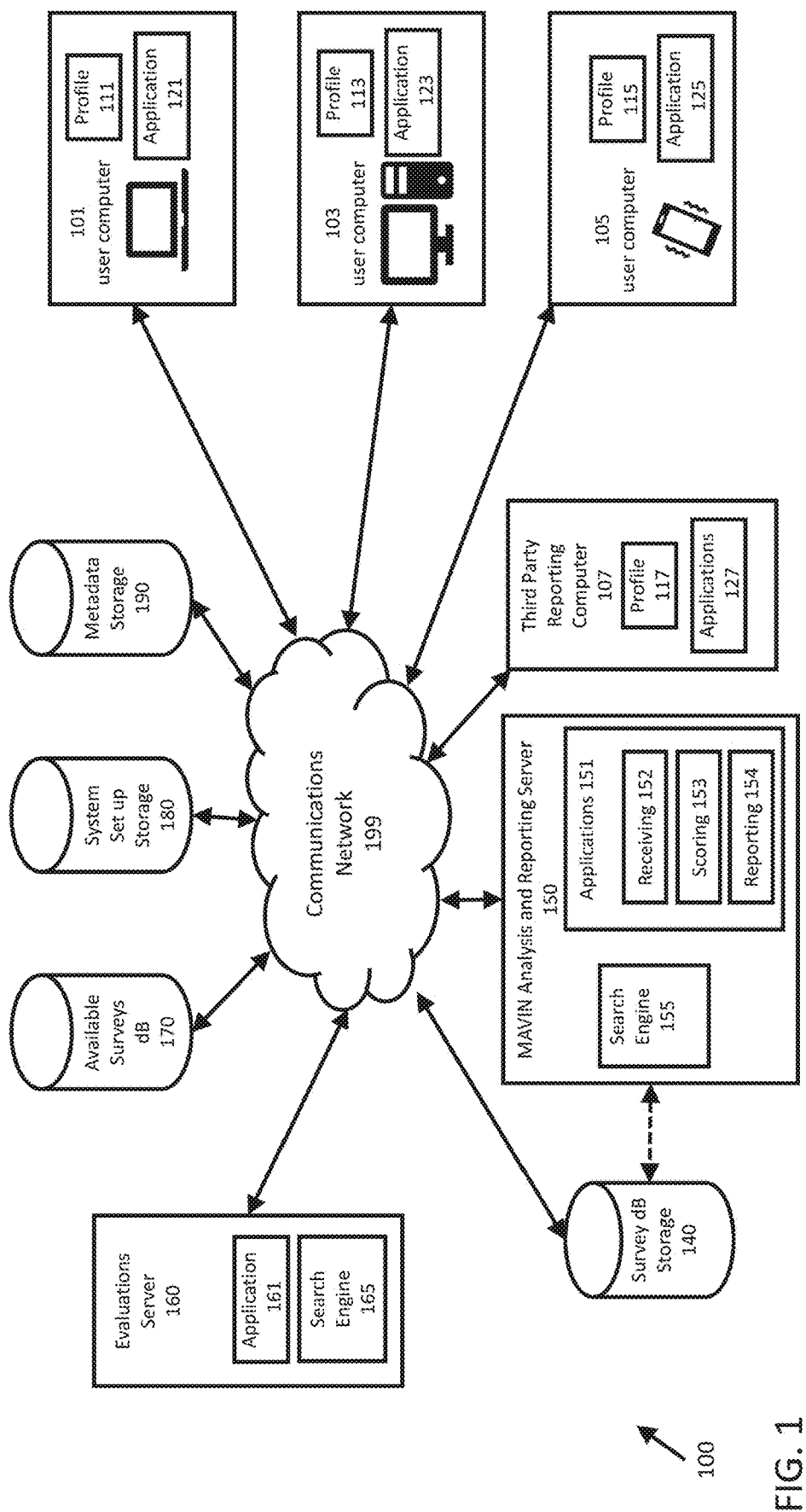
FIG. 1 shows a diagram of an exemplary computer system in accordance with the invention.

The Mavin invention includes a computer-based system for storing, scoring, analyzing, displaying, and reporting results from surveys, interviews, questionnaires, and other evaluative instruments. One example embodiment of the invention uses Five-Option Likert scales as the format for presenting and answering questions. For the purposes of consistency and clarity, the examples in this section use the same Five-Option Likert scale for satisfaction. The format of these questions follows the general structure of, "How satisfied are you with . . . ", and the responses are Very Satisfied (5.00), Satisfied (4.00), Neutral (3.00), Dissatisfied (2.00), and Very Dissatisfied (1.00). The numbers in the parentheses are the segment values for each of the five options. The systems and methods in accordance with the Mavin invention analyze and extract information from these questions, answers, and surveys and reports results that are valid, reliable, actionable, and easy to understand and interpret. The invention described in this disclosure provides a technological solution in improved systems and methods for receiving, analyzing, reporting, and visualizing survey responses and results from a wide array of sources.

One straightforward way to demonstrate methods in accordance with the Mavin invention is to compare two deliveries of the same survey, such as a customer satisfaction survey for two fast food restaurants. In this simplified example, responses to the question, "How satisfied are you with the quality of the salad bar?" are compared. For simplicity, in this example, all of the respondents from both restaurants answered either Very Satisfied or Satisfied. Table 3 displays the results.

TABLE 3

| | "How satisfied are you with the quality of the salad bar?" | | | | | | |
|---|---|---|---|---|---|---|---|
| | Very Satisfied | Satisfied | Neutral | Dissatisfied | Very Dissatisfied | Combined Percent Satisfied (CPS) | Mavin Score (mean) |
| Segment Value | 5.00 | 4.00 | 3.00 | 2.00 | 1.00 | | |
| Restaurant A | 60 | 40 | 0 | 0 | 0 | 100% | 4.60 |
| Restaurant B | 15 | 85 | 0 | 0 | 0 | 100% | 4.15 |

As noted above, the CPS fails to discern any difference between the two restaurants. Inspection of the raw data clearly indicates that the customers of Restaurant A are far more satisfied than the customers of Restaurant B. But how much more satisfied are the customers of Restaurant A? The clear indication can be noted in the number of Very Satisfied customers for Restaurant A. Since there are 100 respondents for each of the restaurants surveyed, it is easy to see that 60% of the Restaurant A customers are Very Satisfied (i.e., 60 respondents out of the total of 100 respondents), and 15% of Restaurant B customers are Very Satisfied (i.e., 15 respondents out of the total of 100 respondents). Therefore, Restaurant A has 45% more Very Satisfied customers than Restaurant B. By using the methods of the Mavin invention, those assessing the results of the surveys can discern this 45% difference from the Mavin Score.

The systems and methods of the Mavin invention view the mean differently compared to other evaluation techniques, and in doing so, gain additional insights into the survey results. For example, for the two restaurants above, the invention identifies the Mavin Score as a single weighted evaluation metric represented in decimal notation, including an integral part and a fractional part. In Table 3 above, the integral part of the Mavin Score for both Restaurant A and Restaurant B is 4, and the fractional part of the Mavin Score for Restaurant A is 60 and for Restaurant B is 15. These fractional values are exactly equal to the percent Very Satisfied for each of the two restaurants. In fact, when all survey respondents select Satisfied or Very Satisfied, the fractional part of the Mavin Score (i.e., the two numerals to the right of the decimal point) is always exactly equal to the percent of respondents who are Very Satisfied. When comparing survey results, subtracting the lower value fractional part (e.g., 15 from the Mavin Score of Restaurant B) from the higher value fractional part (e.g., 60 from the Mavin Score of Restaurant A) always equals the relative difference in the percent of Very Satisfied customers. This is precisely what we are looking for in a metric and what is missing with other systems and methods such as the CPS.

The exemplary implementations of systems and methods of the Mavin invention work well with the simplified example of Table 3. This restrictive condition where all respondents select Satisfied or Very Satisfied is not likely to occur very often. These more realistic survey results are presented in Table 4, where it is instantly apparent that the fractional part of the Mavin Score (i.e., the two numerals to the right of the decimal point) are no longer exactly equal to the percent Very Satisfied.

TABLE 4

"How satisfied are you with the size of the tacos?"

|  | Very Satisfied | Satisfied | Neutral | Dissatisfied | Very Dissatisfied | Combined Percent Satisfied (CPS) | Mavin Score (mean) |
| --- | --- | --- | --- | --- | --- | --- | --- |
| Segment Value | 5.00 | 4.00 | 3.00 | 2.00 | 1.00 |  |  |
| Restaurant X | 40 | 40 | 10 | 5 | 5 | 80% | 4.05 |
| Restaurant Y | 60 | 20 | 10 | 10 | 0 | 80% | 4.30 |
| Restaurant Z | 25 | 55 | 20 | 0 | 0 | 80% | 4.05 |

For Restaurant X, 40% of its customers selected Very Satisfied, but the fractional part of the Mavin Score (i.e., the two numerals to the right of the decimal point) is 05, not 40. The same is true for the other two restaurants' results, with the fractional parts of the Mavin Scores equaling 30 and 05, respectively. Upon further inspection of the data, it is clear that the satisfaction levels of the customers of the three restaurants are not equivalent, but the CPS is exactly the same for all three. As indicated above, the CPS score does not provide accurate insight into the true differences among these businesses.

Using the Mavin Score in systems and methods of the invention provides robust and accurate analyses to identify which restaurant's tacos best satisfy their customers. In addition, it displays the relative difference in their levels of satisfaction. Exemplary implementations of systems and methods of the Mavin invention treat the Five-Option Likert scale as an interval scale, and combine those methods with its treatment of the mean score to provide accurate analyses that lead to valuable insights. Other systems and methods of analysis and display fail in their ability to make such nuanced judgments.

In Table 4 again, Restaurant Z is shown to have 25% of its customers responding that they are Very Satisfied (i.e., twenty-five respondents selected Very Satisfied out of one hundred total respondents), and 20% are Neutral (i.e., twenty respondents selected Neutral out of one hundred total respondents). By treating the respondent data as an interval scale, the difference between a Very Satisfied customer and a Satisfied customer equals+1, and the difference between a Satisfied customer and a Neutral customer is −1. Very Satisfied is one segment greater than Satisfied, and Neutral is one less than Satisfied. The Mavin invention identifies the respondent data on an interval scale and analyzes the responses about the defensible standard score.

As noted above, in some exemplary embodiments of the invention, the Mavin systems and methods define the defensible standard as when all customers indicate that they are Satisfied. If all respondents indicate that they are satisfied, the conclusion would be that the restaurant met the standard. Since Satisfied is valued at 4.00, the defensible standard is set to the value of 4.00.

The Mavin invention analyzes those responses to either side of the defensible standard score. In this simplified example, the invention subtracts the percentage of Neutral respondents (20%) from the percentage of Very Satisfied respondents (25%) which results in a difference of 5%. This is exactly equal to the fractional part of the Mavin Score (i.e., the two numerals to the right of the decimal point).

A defensible standard can be used to judge assessments, perceptions, and attitudes of individuals, as well as for making valid comparisons between, amongst, and within different respondents or groups of respondents. In addition, it can measure the degree of difference between two competing entities.

System Overview

Example embodiments of the invention feature systems and methods for analyzing and aggregating survey research data. FIG. 1 shows a block diagram of a computer-based system 100 for storing, scoring, analyzing, and reporting results from psychometric instruments. System 100 includes communications network 199. Communications network 199 is the medium used to provide communication links between several; devices and computers connected together within the system 100. Communications network 199 can include connections, such as wire, wireless communication links, or fiber optic cables, from individual clients, servers, databases, sources of data, and processing components. The clients, servers, data, and processing components can access the communication network 199 using a variety of software architectural frameworks, web services, file transfer protocols, and Internet exchange points. Communications network 199 can represent a collection of networks and gateways that use the Transmission Control Protocol/Internet Protocol (TCP/IP) and other communication protocols, as well as application programming interfaces (APIs), to communicate with one another and with devices connected to the network 199. One example communications network 199 includes the Internet, which can include data communication links between major nodes and/or host computers, including thousands of commercial, governmental, educational, and other computer systems that route data and messages. FIG. 1 is one example of an environment of an exemplary embodiment of the invention and is not an architectural limitation for different illustrative embodiments of the invention. sources Clients and servers are only example roles of certain data processing systems and computer systems connected to communications network 199 which do not exclude other configurations or roles for these data processing systems. Mavin analysis and reporting server 150 and Psychometric evaluations computer 160 connect to data exchange network 199 along with Available Surveys dB 170, System set up storage (dB) 180, and Metadata storage (dB) 190 (all of which can include servers, databases, processors, and the necessary software and hardware to execute applications and methods for acquiring and sending surveys, system set up information, and metadata as well as other files and data to execute applications and methods of the invention). Software applications can execute on any computer in the system 100. User computers (e.g., clients), including user computers 101, 103, and 105 are also connected to communications network 199. A data processing (computer) system, such as servers 150, 160 and clients 101, 103, 105, and databases and data sources 140, 160, 170, 180, 190 (and other connected devices) can include data and can have software applications and/or software tools executing on them.

FIG. 1 displays an example of a system architecture and shows certain components that are usable in an exemplary embodiment of the invention. For example, servers 150, 160 and clients 101, 103, 105 are depicted as servers and clients only as example and not to imply a limitation to a client-server architecture. In another exemplary embodiment of the invention, the system 100 can be distributed across several data processing (computer) systems and a data network as shown. Similarly, in another exemplary embodiment of the invention, the system 100 can be implemented on a single data processing system within the scope of the illustrative embodiments. Data processing (computer) systems 101, 103, 105, 140, 150, 160, 170, 180, 190 also represent example nodes in a cluster, partitions, and other configurations suitable for implementing an exemplary embodiment of the invention.

The computers (e.g., 101, 103, 105) can take the form of a smartphone, a tablet computer, a laptop computer, a desktop computer, a wearable computing device, or any other suitable computing device and the computers (e.g., 140, 150, 160, 170, 180, 190) can be servers, personal computers, and/or network computers. Software application programs described as executing in the system 100 in FIG. 1 can be configured to execute in user computers in a similar manner. Data and information stored or produced in another data processing system can be configured to be stored or produced in a similar manner.

Applications 111, 131, 151 implement an exemplary embodiment or function of the invention as described in this disclosure. For example, dynamic credit limit application 131 receives a request from an application 111 on supplier computing device 110, including payment information such as currency, payment dates, selected invoices, and other supplier information. Applications 121, 123, 125, 127 of the user computers (and third-party computers 107) implement an embodiment or a function as described to operate in conjunction with applications 151, 161 on the Mavin analysis and reporting server 150 and psychometric evaluations computer 160. For example, application 121 provides the user profile information used by psychometric evaluations computer application 161 to process and identify survey information to be sent to and analyzed by Mavin analysis and reporting server application 151. Similarly, psychometric evaluations computer 160 and application 161 operates in conjunction with application 151 on the Mavin analysis and reporting server 150 and provides survey results and records used by the Mavin analysis and reporting application 151 to process, identify, analyze, and report actionable survey findings to users 101, 103, 105 and third parties 107.

Computers 101, 103, 105, 107, 140, 150, 160, 170, 180, 190 and additional computers (e.g., clients and servers), may couple to communication network 199 using wired connections, wireless communication protocols, or other suitable data connectivity.

In the depicted example, Mavin Analysis and Reporting server 150 may provide data, such as boot files, operating system images, and applications to user computers (clients and servers) 101, 103, 105, 107. Clients 101, 103, 105, 107 may be clients to server 150 in this example. Client 101, 103, 105, 107 and servers 140, 150, 160, 170, 180, 190, or some combination, may include their own data, boot files, operating system images, and applications. System 100 may include additional servers, clients, and other devices that are not shown. For example, while countless users and databases can be used to provide survey inputs to the analysis and reporting server using systems and methods constructed according to the principles and exemplary embodiments of the invention, for clarity and brevity, three distinct user computers are shown with a single psychometric evaluations computer 160, a third-party reporting computer 107, and individual discrete databases 140, 170, 180, 190 as shown in FIG. 1.

Among other uses, system 100 may be used for implementing a client-server environment in accordance with exemplary embodiments of the invention. A client-server environment enables software applications and data to be distributed across a network such that an application functions by using the interactivity between a user computer and a server. System 100 may also employ a service-oriented architecture, where interoperable software components distributed across a network can be packaged together as coherent applications.

Together, the system 100 provides inputs for the Mavin analysis and reporting server application 151 to receive, process, analyze, classify, and provide actionable intelligence and recommendations. The system 100 uses inputs from psychometric evaluations computer server 160 as further inputs for the Mavin analysis and reporting application 151. Additionally, databases and data sources 140, 160, 170, 180, and 190 provide fast data in real-time for use in analyzing and reporting survey results and recommendations, respectively. As inputs and results from user computers 101, 103, 105, psychometric evaluations computer 160, and databases and sources of fast data 140, 170, 180, 190 are received, analysis and reporting server 150 and application 151 reassess and redetermine the actionable recommendations.

As will be appreciated by one skilled in the art, aspects of the disclosure may be embodied as a system, method, or computer program product. Accordingly, aspects of the disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, or any suitable combination. Computer program code for carrying out operations for aspects of the disclosure may be written in any combination of one or more programming languages, including an object-oriented programming language such as Java, Smalltalk, C++ or the like and conventional procedural programming languages, such as the "C" programming language or similar programming languages. Other types of programming languages include HTML5, Flash and other similar languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of communications network, including a local area network (LAN) or a wide area network (WAN), or the connection may be made to an external computer (for example, through the Internet using an Internet Service Provider).

Aspects of the invention are described in this disclosure with reference to flowchart illustrations and/or block diagrams of methods, apparatus (systems) and computer program products according to exemplary embodiments of the invention. Each block of the flowchart illustrations and/or block diagrams, and combinations of blocks in the flowchart illustrations and/or block diagrams, can be implemented by computer program instructions. These computer program instructions may be provided to a processor of a server, or other programmable data processing apparatus to produce a machine, such that the instructions, which execute via the processor of the server or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams, as shown in this disclosure, illustrate the architecture, functionality, and operation of possible implementations of systems, methods, and computer program products according to various exemplary embodiments of the invention. In this regard, each block in the flowchart or block diagrams may represent a module, segment, or portion of code, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

For clarity and consistency, this disclosure describes an exemplary embodiment of an analysis and reporting system in accordance with the invention as it applies to a Five-Option fully anchored Likert scale for satisfaction (Very Satisfied, Satisfied, Neutral, Dissatisfied, and Very Dissatisfied). There are other Five-Option Likert scales relating to agreement, importance, etc. The Mavin systems process and analyze these other scales in a similar manner. For example, in analyzing and reporting, other exemplary systems of the invention may change the labels from Very Satisfied to Strongly Agree.

In some exemplary embodiments of the invention, Likert scales with three, four, six, and seven options are analyzed and reported using a similar approach with only minor changes.

The systems and methods of the Mavin invention differ from traditional Likert analyses by treating the responses as interval data rather than ordinal data. As mentioned above, each of the five levels of satisfaction is assigned a numeric segment value. Very Dissatisfied is assigned the segment value of one (1.00), Dissatisfied is assigned the segment value of two (2.00), Neutral is assigned the segment value of three (3.00), Satisfied is assigned the segment value of four (4.00), and Very Satisfied is assigned the segment value of five (5.00).

The treatment of Likert scales as interval scales is not universally endorsed. Traditional psychometric analyses treat Likert scales as ordinal, claiming that the five levels (e.g., segments) of responses may not form equal intervals. To address this, the systems and methods of the Mavin invention include a mechanism to adjust these segment values when there is compelling evidence that the true measure of one or more of responses differs from the assigned segment values. For example, if a company finds that Very Dissatisfied customers are far more likely to stop doing business than merely Dissatisfied customers, the segment value for Very Dissatisfied can be adjusted by assigning a value lower than 1.00, such as 0.75. Likewise, if Neutral customers are found to be only slightly more likely to stop doing business than Satisfied customers, the segment value of 3.00 can be adjusted upward to 3.50, for example, for Neutral responses.

Example System Operation

Figure 2:
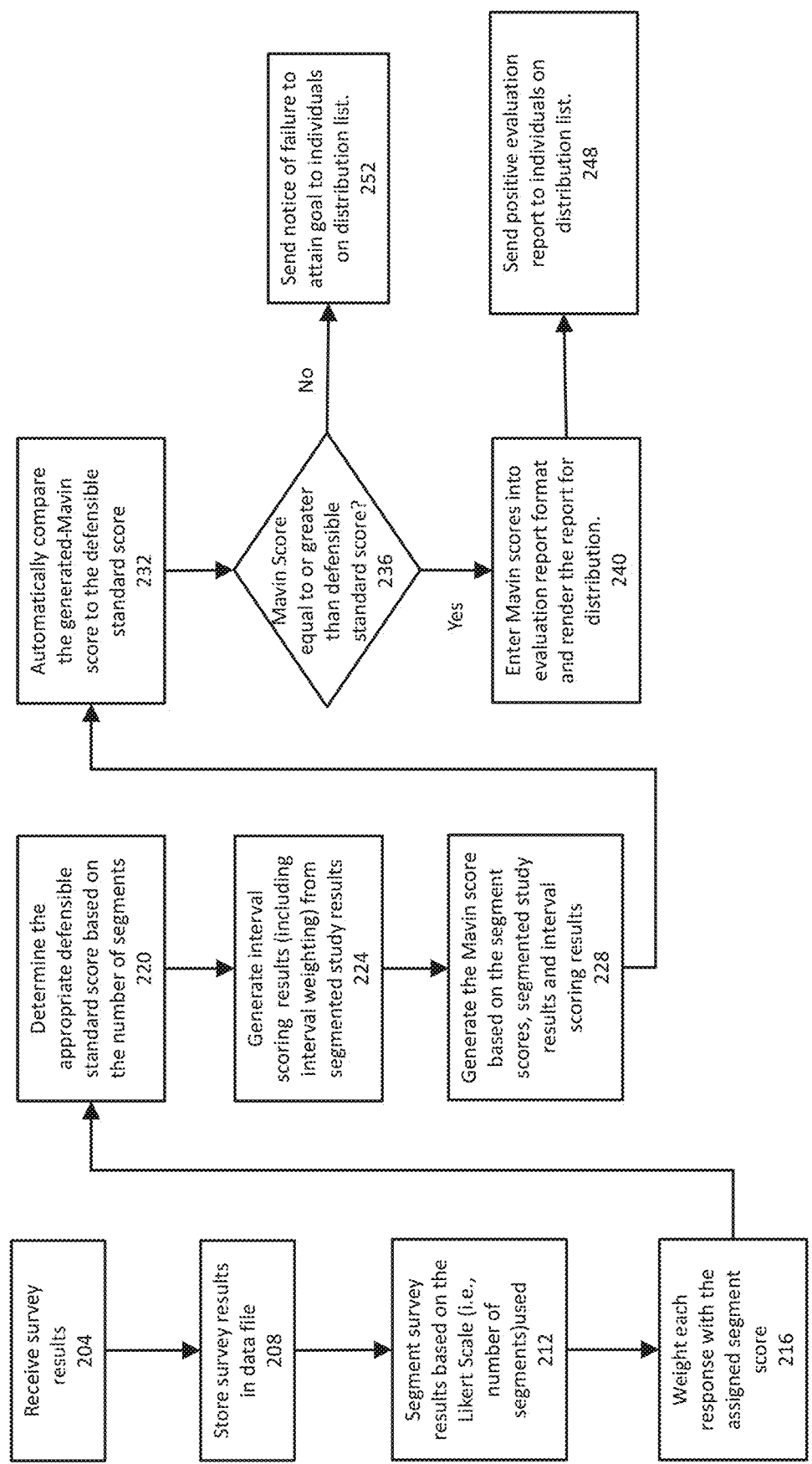
FIG. 2 is a process flow chart of an exemplary method carried out by a system in accordance with the invention.
Figure 3:
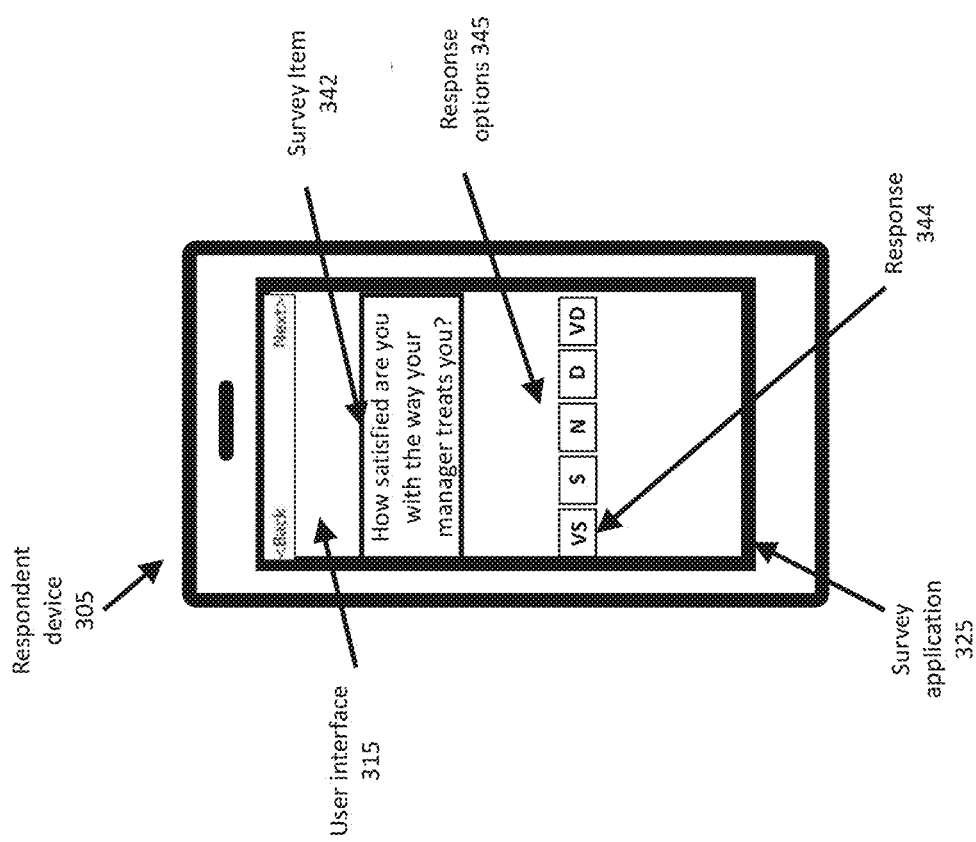
FIG. 3 shows an example graphical user interface of a respondent device according to an exemplary embodiment of the invention.

As shown in an exemplary method in FIG. 2, a Mavin system receives, in block 204, a set of responses to survey questions using a Five-Option Likert scale. In block 208, the systems of the invention store the study results. For example, compiled study results can be received from evaluations server 160 or the study results can be acquired directly from a respondent device (such as users 101, 103, 105). FIG. 3 shows an example user interface 315 for a respondent device 305 according to an example embodiment. In the exemplified embodiment, the respondent device 305 is a mobile smartphone. As outlined above, in other embodiments, the respondent device 305 can be any computer device capable of carrying out programs in accordance with the functions described in this disclosure (including laptop computers, desktop computers, and tablets, for example). In other example embodiments, a more traditional survey system can be used.

The user interface 315 of an example respondent device 305 shows a first instance of a survey application 325. In the exemplified embodiment, the survey application 325 is a smartphone application. In other embodiments, the survey application 325 can be any program for carrying out the functions described in this disclosure. The respondent device 305 provides the respondent user interface 315. In the exemplified embodiment, the user interface 315 utilizes a touch screen provided by the smartphone. In other embodiments, the user interface can be any user interface capable of enabling a user to communicate with and carry out the functions described in this disclosure, including an interface utilizing a computer monitor, mouse, and/or keyboard. The respondent user interface 315 shows a survey item 342, namely, "How Satisfied Are You with the Way Your Manager Treats You?" The respondent user interface 315 provides response options 345 for a response. In the exemplified embodiment, there are five scale response options 345 to choose from (corresponding to a Five-Option Likert Survey). The response options 345 include from left to right: VS (Very Satisfied), S (Satisfied), N (Neutral), D (Dissatisfied), and VD (Very Dissatisfied). The scale response options 345 represent different ratings of how the respondent's manager is treating the respondent. In some embodiments of the invention, the response options may be selected using a slider either to select the discrete response options, or to select a response that is between two adjacent response options. In the exemplified embodiment, the VS option has been chosen as the response 344. In other embodiments, other rating options having other meanings can be available.

Returning to FIG. 2, in block 212, the processes continue as the study results are segmented into a fully anchored scale with a predetermined number of segments. In this example, there are five segments corresponding to the five options on the Likert scale. In block 216, the system weights each segment with a segment value. In a five-option Likert scale, this weighting is often 5.0 for very satisfied, 4.00 for satisfied, 3.00 for neutral, 2.00 for dissatisfied, and 1.00 for very dissatisfied. However, as outlined above the weighting can be modified based on input and evidence from the source of the survey, the organization, and other parties. In block 220, the system determines a defensible standard score based on the number of predetermined segments and the segment values. In block 224, the system extracts the interval scoring data from the segmented study results.

In block 228, the systems of the Mavin invention compute the arithmetic mean (i.e., the Mavin Score) of the assigned values. By using the mean value in place of the CPS, the Mavin systems and methods address the shortcomings of prior systems outlined above. The Mavin systems and methods differentiate each of the anchored response options from the others when calculating the results. Further, the Mavin systems and methods provide a valid, easily interpretable, method for discerning the degree of difference/lack of difference within respondents.

In block 232, the Mavin systems and methods automatically compare the generated Mavin Score to the defensible standard score. The defensible standard score is the benchmark for judging the performance of individuals (or organizations, groups, etc.), as well as for making valid comparisons of respondents, and of respondent answers. In block 236, the systems and methods of the invention determine whether the Mavin Score is equal to or greater than the defensible standard score in which case the reporting application enters the Mavin Score into a customizable evaluation report format and renders the report for distribution in block 240. In block 248, the reporting application automatically sends the positive evaluation report to recipients on a distribution list. On the other hand, in block 236, when the systems and methods of the invention determine that the Mavin Score is less than the defensible standard score, in block 252 the reporting application enters the Mavin Score into a customizable evaluation report format, renders the report for distribution, and automatically sends the failure to attain goal evaluation report to recipients on a distribution list.

The exemplary embodiments of computer-based Mavin systems for storing, scoring, analyzing, and reporting results from psychometric instruments that use fully anchored Likert scales score the survey results using a different segment value for each of the anchored options. The systems generate valid, reliable, easily interpretable results, capable of discerning the degree of difference between the scores from two or more individuals or from multiple groups taking a survey. In addition, the systems and methods of the invention support the designation of a defensible standard (i.e., benchmark) for judging results using the above score.

As outlined above, for each Five-Option Likert scale question, the systems and methods of the invention compute the Mavin Score of the assigned segment values for the five levels of satisfaction. This operation addresses the limitation inherent in using the CPS as the measure of satisfaction, which combines Very Satisfied and Satisfied into the single category of Satisfied and/or may combine Neutral, Dissatisfied, and Very Dissatisfied into a single category of Not Satisfied. As noted above, ignoring the difference between Satisfied and Very Satisfied masks the "enthusiasm level" which is expressed by respondents who answered Very Satisfied. Combining Neutral, Dissatisfied, and Very Dissatisfied similarly masks the extent of the loss of good will from the Dissatisfied and Very Dissatisfied respondents. Losing either of these capabilities can greatly decrease the power of the subsequent analysis to inform decisions.

These differences can be far from trivial. For example, two managers are considered for promotion. The selection committee chooses to base their decision on the results of a company-wide employee survey, specifically the question, "How satisfied are you with the way your manager treats you?" Table 5 below displays the results of the survey. The CPS for the two candidates shows no difference. However, the Mavin Score strongly, and accurately, favors Manager A.

TABLE 5

"How satisfied are you with the way your manager treats you?"

|  | Very Satisfied | Satisfied | Neutral | Dissatisfied | Very Dissatisfied | Combined Percent Satisfied | Mavin Score |
|---|---|---|---|---|---|---|---|
| Segment Value | 5.00 | 4.00 | 3.00 | 2.00 | 1.00 | | |
| Manager A | 60 | 30 | 7 | 3 | 0 | 90% | 4.47 |
| Manager B | 15 | 75 | 4 | 4 | 2 | 90% | 3.97 |

Comparisons using the CPS would find no difference between the ratings of the two managers, whereas the Mavin Score indicates that Manager A is by far the better candidate.

A second distinction between the systems and methods of the invention and previous systems concerns the CPS's lack of ability to make comparative judgments between two or more sets of survey results. For example, a national restaurant chain is looking to promote one of three local restaurant managers to regional manager. Table 6 below displays the overall satisfaction of surveyed customers from the three restaurants. Using the CPS, the manager of Restaurant C is the clear winner. However, inspection of the underlying data and the resultant Mavin Scores make a much stronger case for promotion of the manager of Restaurant A. The CPS lacks the ability to distinguish the differences between the two levels of satisfaction and among the three levels that are less than Satisfied (i.e., Neutral, Dissatisfied, and Very Dissatisfied), limiting the ability to identify the true differences. These analysis and reporting errors do not occur when using the Mavin Scores.

TABLE 6

Overall Customer Satisfaction with the Dining Experience

|  | Very Satisfied | Satisfied | Neutral | Dissatisfied | Very Dissatisfied | Combined Percent Satisfied (CPS) | Mavin Score |
|---|---|---|---|---|---|---|---|
| Segment Value | 5.00 | 4.00 | 3.00 | 2.00 | 1.00 | | |
| Manager of Restaurant A | 60 | 30 | 7 | 3 | 0 | 90% | 4.47 |
| Manager of Restaurant B | 45 | 47 | 5 | 2 | 1 | 92% | 4.36 |
| Manager of Restaurant C | 19 | 75 | 4 | 1 | 1 | 94% | 4.10 |

An additional capability and benefit of the systems and methods of the invention is the ability to support the designation of an accepted benchmark. The CPS has been shown to lack the quantitative underpinnings to support such a benchmark. For example, a chain of automotive parts stores routinely surveys its customers. The senior management team chooses to award bonuses to employees of stores with high levels of customer satisfaction. The CPS level is set to 90% as the standard to qualify for the bonuses. Table 7 below displays survey results from three stores, two of which meet the CPS standard. However, examining the underlying data and the resultant Mavin Scores shows that the CPS is not an appropriate metric to set a standard. Store A received a CPS score of 89%; thus, the employees of Store A would not receive the bonus. However, adopting the Mavin Score to set the benchmark, management discovers that, of the three stores, Store A's customers are actually the most satisfied.

TABLE 7

Customer Satisfaction with Three Automotive Parts Stores

|  | Very Satisfied | Satisfied | Neutral | Dissatisfied | Very Dissatisfied | Combined Percent Satisfied (CPS) | Mavin Score |
|---|---|---|---|---|---|---|---|
| Segment Value | 5.00 | 4.00 | 3.00 | 2.00 | 1.00 | | |

TABLE 7-continued

Customer Satisfaction with Three Automotive Parts Stores

|  | Very Satisfied | Satisfied | Neutral | Dissatisfied | Very Dissatisfied | Combined Percent Satisfied (CPS) | Mavin Score |
|---|---|---|---|---|---|---|---|
| Store A | 60 | 29 | 8 | 3 | 0 | 89% | 4.46 |
| Store B | 35 | 57 | 5 | 2 | 1 | 92% | 4.23 |
| Store C | 17 | 73 | 3 | 4 | 3 | 90% | 3.97 |

Given its ability to fully address these concerns and provide additional analytical capabilities, using the Mavin Score in lieu of the CPS is compelling, and at first glance, it would seem that setting a defensible score (benchmark) as the value obtained if all customers were to select Satisfied is most appropriate. In that case, the Mavin Score would be 4.00. The analysis changes, however, when customers select responses other than Satisfied. The systems and methods of the invention automatically determine a defensible standard score based on the number of segments and the segment values. For example, the Mavin Score is adjusted when customers select responses other than Satisfied. The Mavin Score determination identifies characteristics of an interval scale to automatically make these adjustments. Since Very Satisfied is one unit above Satisfied and Neutral is one unit below Satisfied, the standard can be met if every Neutral response is balanced with a Very Satisfied response. Table 8 below presents this scenario.

TABLE 8

Equivalence of Very Satisfied Responses and Neutral Responses

|  | Very Satisfied | Satisfied | Neutral | Dissatisfied | Very Dissatisfied | Row Totals | Mavin Score |
|---|---|---|---|---|---|---|---|
| Segment Value | 5.00 | 4.00 | 3.00 | 2.00 | 1.00 | — | — |
| N (number of respondents with this segment value) | 15 | 70 | 15 | 0 | 0 | 100 | — |
| N x Value | 75 | 280 | 45 | 0 | 0 | 400 | 4.00 |

Of 100 surveyed respondents listed in Table 8, fifteen (15) chose Very Satisfied, 70 chose Satisfied, and 15 chose Neutral. As noted above, the equivalence of responses for Very Satisfied and Neutral result in a Mavin Score of 4.00, maintaining equality to the standard and equal intervals between responses.

Table 9 below displays the equivalence of 2 Very Satisfied responses for each Dissatisfied response.

TABLE 9

Equivalence of 2 Very Satisfied Responses for each Dissatisfied Response

|  | Very Satisfied | Satisfied | Neutral | Dissatisfied | Very Dissatisfied | Row Totals | Mavin Score |
|---|---|---|---|---|---|---|---|
| Segment Value | 5.00 | 4.00 | 3.00 | 2.00 | 1.00 | — | — |
| N (number of respondents with this segment value) | 10 | 85 | 0 | 5 | 0 | 100 | — |
| N x Value | 50 | 340 | 0 | 10 | 0 | 400 | 4.00 |

Of 100 surveyed respondents listed in Table 9, ten (10) chose Very Satisfied, 85 chose Satisfied, and 5 chose Dissatisfied. As noted above, the equivalence of responses for Very Satisfied and Dissatisfied result in a Mavin Score of 4.00, maintaining equality to the standard.

Extending this comparison, Table 10 below displays the equivalence of 3 Very Satisfied responses for each Very Dissatisfied response.

TABLE 10

Equivalence of 3 Very Satisfied Responses for each Very Dissatisfied Response

|  | Very Satisfied | Satisfied | Neutral | Dissatisfied | Very Dissatisfied | Row Totals | Mavin Score |
|---|---|---|---|---|---|---|---|
| Segment Value | 5.00 | 4.00 | 3.00 | 2.00 | 1.00 | — | — |
| N (number of respondents with this segment value) | 9 | 88 | 0 | 0 | 3 | 100 | — |
| N x Value | 45 | 352 | 0 | 0 | 3 | 400 | 4.00 |

Of 100 surveyed respondents listed in Table 10, nine (9) chose Very Satisfied, 88 chose Satisfied, and 3 chose Very Dissatisfied. As noted above, the equivalence of responses for Very Satisfied and Very Dissatisfied result in a Mavin Score of 4.00, maintaining equality to the standard.

Table 11 displays the equivalence when all 5 of the response options are included.

TABLE 11

Equivalence of All 5 of the Response Options

|  | Very Satisfied | Satisfied | Neutral | Dissatisfied | Very Dissatisfied | Row Totals | Mavin Score |
|---|---|---|---|---|---|---|---|
| Segment Value | 5.00 | 4.00 | 3.00 | 2.00 | 1.00 | — | — |
| N (number of respondents with this segment value) | 12 | 80 | 5 | 2 | 1 | 100 | — |
| N x Value | 60 | 320 | 15 | 4 | 1 | 400 | 4.00 |

Of 100 surveyed respondents listed in Table 11, twelve (12) chose Very Satisfied, 80 chose Satisfied, 5 chose Neutral, 2 chose Dissatisfied, and 1 chose Very Dissatisfied. The equivalence of responses results in a Mavin Score of 4.00, maintaining equality to the standard.

As noted above, the Mavin processes include the ability to adjust its calculations when there is compelling evidence that the assumption of equal/linear spacing of the five segments of satisfaction fails to hold true. For instance, a business might observe that customers who indicate they are Very Dissatisfied are far more likely to cancel service than those who are merely Dissatisfied. In such cases, the segment value of Very Dissatisfied can be adjusted to reflect that empirical difference.

For example, the XYZ Insurance Company bases its employee bonuses on customer satisfaction, specifically their answers to the following question on a survey sent to every customer: "Overall, how satisfied are you with the service you receive from XYZ Insurance?" XYZ's senior management team uses the systems and methods of the Mavin invention to analyze the results, and have adopted the Mavin Score of 4.00 as the benchmark. As a quality check, the management team elected to see how actual policy cancellations related to customer satisfaction as indicated on the survey. For each segment of satisfaction, the percentage of customers who, within a year, cancelled their policy was determined. Those values were added to the data file, and the option to include them in the report as an adjusted Mavin Score was selected. Table 12 depicts how these simplified adjustments were processed.

In this example, the evidence includes records and findings that customers who are Very Dissatisfied with the service they receive from XYZ Insurance are far more likely to cancel their service than customers who are Dissatisfied. Table 12 below shows the measured probability of customers that cancel their service for each segment of overall satisfaction. Row 3 shows customers who are Very Satisfied with their service cancel 1.2% of the time. Similarly, customers who are Satisfied with their service cancel 2.3% of the time, and customers who are Neutral with their service cancel 5.6% of the time. Customers who are Dissatisfied with their service cancel 10.0% of the time, and customers who are very Dissatisfied cancel 29.3% of the time.

TABLE 12

Adjustment for Non-Linear Intervals

| Row |  | Col. 1 | Col. 2 | Col. 3 | Col. 4 | Col. 5 |  |  |
|---|---|---|---|---|---|---|---|---|
| 1 | 1. Response Segment | VS | S | N | D | VD | Total N | Mavin |
| 2 | 2. Number of responses (N) | 505 | 255 | 85 | 70 | 85 | 1,000 | Scores |
| 3 | 3. Percent of Customers Cancelling Their Policy | 1.2% | 2.3% | 5.6% | 10.0% | 29.3% | Row |  |
| 4 | 4. Relative Change in % of Customers Cancelling | N/A | 1.9 | 2.4 | 1.8 | 2.9 | Totals |  |
| 5 | 5. Normalized Change in % of Customers Cancelling | N/A | 1.0 | 1.3 | 0.9 | 1.5 |  |  |

TABLE 12-continued

Adjustment for Non-Linear Intervals

| Row | | Col. 1 | Col. 2 | Col. 3 | Col. 4 | Col. 5 | | |
|---|---|---|---|---|---|---|---|---|
| 6 | 6. Assigned Response Segment Value | 5.00 | 4.00 | 3.00 | 2.00 | 1.00 | | |
| 7 | 7. Adjusted Response Segment Value | 5.00 | 4.00 | 2.87 | 2.22 | 0.50 | | |
| 8 | 8. Standard Mavin Score | 2,525 | 1,020 | 255 | 140 | 85 | 4,025 | 4.03 |
| 9 | 9. Adjusted Mavin Score | 2,525 | 1,020 | 244 | 155 | 43 | 3,987 | 3.99 |
| 7 | 7. Adjusted Response Segment Value | | | 2.87 | 2.22 | 0.43 | | |
| 7 | 7. Adjusted Response Segment Value-limited | | | 2.87 | 2.22 | 0.50 | | |
| 10 | Limit to adjustments +/− | | | 0.50 | 0.50 | 0.50 | | |
| 11 | Reference Interval for Relative Change in Customers Cancelling | | | 1.9 | | | | |

The first three rows of Table 12 are determined as outlined above. For example, row 1 of Table 12 describes the Response Segments, where VS is Very Satisfied, S is Satisfied, N is Neutral, D is Dissatisfied, VD is Very Dissatisfied, and Total N is the heading for the total Number of Responses in row 2. (i.e., the sum of the number of responses for each response segment).

Row 2 of Table 12 shows the number of survey responses for each of the Response Segments. There are 505 Very Satisfied responses, 255 Satisfied responses, 85 Neutral responses, 70 Dissatisfied responses, and 85 Very Satisfied responses, for a total (Total N) of 1,000 responses.

Row 3 of Table 12 shows the percent of customers cancelling their policy within a year of filling out the survey. This evidence-based percentage comes from matching the survey respondents' satisfaction ratings to XYZ Company's internal cancellation records. Based on the actual cancellation records, the respective percentages were for Very Satisfied, 1.2%; Satisfied, 2.3%; Neutral, 5.6%; Dissatisfied, 10.0%; and Very Dissatisfied, 29.3%.

The systems and methods of the invention determine the relative change in the percent of customers cancelling between each of the segments. That is, the relative change in percent of customers cancelling is calculated by comparing the percent cancelling for the current response segment to the percent of customers cancelling in the next higher response (i.e., left adjacent) segment. For example, row 4 of Table 12 displays the relative change in the percent of customers cancelling their policy for each of the 5 Response Segments. Row 4 values are determined from the value of the same segment in row 3, divided by the value in the left adjacent segment in row 3. Since there is no left adjacent segment for Very Satisfied, the relative change is not available (N/A) for that row 4 segment. Thus, no adjustment is made. In this simplified example, relative change in the percent of Satisfied customers cancelling their policy is determined by dividing the percent of Satisfied Customers cancelling their policy (row 3, column 2) by the percent of Very Satisfied Customers cancelling their policy (row 3, column 1), that is, 2.3%÷1.2%=1.9. This is shown in Table 12 when moving from Very Satisfied to Satisfied and as the Reference Interval for Relative Change in Customers Cancelling in row 11 of Table 12. This means that a Satisfied customer is 1.9 times as likely to cancel their policy as would a Very Satisfied customer. Similarly, when moving from Satisfied to Neutral, the relevant change in percent of Neutral customers cancelling is determined by dividing the percent of Neutral customers cancelling (5.6%) (row 3, column 3) by the percent of Satisfied customers cancelling (2.3%) (row 3, column 2), that is, 5.6%÷2.3%=2.4. That is, Neutral customers are 2.4 times more likely to cancel their service than Satisfied customers. Extending these examples, when moving from Neutral to Dissatisfied, the relevant change in percent of Dissatisfied customers cancelling is determined by dividing the percent of Dissatisfied customers cancelling (10.0%) (row 3, column 4) by the percent of Neutral customers cancelling (5.6%) (row 3, column 3), that is, 10.0%+5.6%=1.8. That is, Dissatisfied customers are 1.80 times more likely to cancel their service than Neutral customers. When moving from Dissatisfied to Very Dissatisfied, the relevant change in percent of Very Dissatisfied customers cancelling is determined by dividing the percent of Very Dissatisfied customers cancelling (29.3%) (row 3, column 5) by the percent of Dissatisfied customers cancelling (10.0%) (row 3, column 4), that is, 29.3%÷10.0%=2.9. That is, Very Dissatisfied customers are 2.9 times more likely to cancel their service than Dissatisfied customers.

To provide further analysis and actionable results, the systems and methods of the invention normalize the change in the percent of customers cancelling. For example, in Table 12, the defensible standard score is 4.0, based on Satisfied customers and provides a basis for the normalization performed by the invention. To illustrate, row 5 is the normalized change in percent of Customers cancelling. For each of the segments (Satisfied, Neutral, Dissatisfied, Very Dissatisfied), the relative change in percent of customers cancelling is compared to the relative change in percent of Satisfied customers cancelling. In the example of Table 12, each of the (row 5) normalized values are determined by dividing the relative change in percent of customers cancelling of that segment (in row 4) by the (row 4) value of the relative change in percent of Satisfied customers cancelling which is 1.9. As expected, because the basis of normalization is the relative change in percent of Satisfied customers cancelling, normalizing this relative change results in a (row 5) value for Satisfied of 1.0 (1.9÷1.9=1.0). The systems and methods of the invention continue and normalize the change in percent of customers cancelling to determine the other (row 5) values relative to the percent of Satisfied customers who cancel. This normalization makes it easier to see the degree to which the responses of the surveyed customers conform to a linear interval scale. In a true linear interval scale, each of the normalized values in the four populated segments in row 5 would be 1.0.

As with the examples above, row 6 of Table 12 shows the Assigned Response Segment values, which for a Five-Option Likert scale is Very Satisfied=5.00, Satisfied=4.00, Neutral=3.00, Dissatisfied=2.00, and Very Dissatisfied=1.00. These values are reflective of a linear interval scale.

However, as outlined in the example above, and as borne out by the evidence considered by the XYZ Company, the percent of customers cancelling for each of the response segments is not linear. To accurately reflect the actual percent of customers cancelling for each of the response segments, the systems and methods of the invention determine an Adjusted Response Segment value.

To determine an Adjusted Response Segment value, the systems and methods of the invention compare the nominal segment values for that segment and the next "higher" segment and the relative changes in the percent of customers cancelling for that segment and for the next "higher" segment. The systems and methods of the invention determine the individual Adjusted Response Segment values for Neutral, Dissatisfied, and Very Dissatisfied by the following relationship (1), which equates to a computer process carrying out (2).

(Assigned Response Segment value for Response Segment of $\text{column}_x$−((Relative Change in Customers Cancelling for Response Segment of $\text{column}_x$−Relative Change in Customers Cancelling for Response Segment of $\text{column}_{x-1}$)÷Assigned Response Segment value for Response Segment of $\text{column}_{x-1}$))    (1)

(Row6 Segment value−((Row4 Segment value−Row4 left adjacent value)÷Row6 left adjacent value))    (2)

The Adjusted Response Segment values are shown in row 7 of Table 12, with Adjusted Response Segment values of 5.00 for Very Satisfied, 4.00 for Satisfied, 2.87 for Neutral, 2.22 for Dissatisfied, and 0.50 for Very Dissatisfied. Users and evaluators can limit the range of adjustment of the Adjusted Response Segment values based on additional evidence, historical analysis, and other empirical factors. For example, row 10 of Table 12 displays a limiting value for the size of the adjustment. That is, the adjustment limits for Neutral, Dissatisfied, and Very Dissatisfied are ±0.50. If an adjustment exceeds this limit, the adjustment is decreased to the limit amount displayed (e.g., ±0.50). The Adjusted Response Segment Value for the Very Dissatisfied segment demonstrates this limit. The formula above set the Adjusted Response Segment Value to 0.43, which is 0.07 more than the 0.50 adjustment limit, so the Adjusted Response Segment Value for the Very Dissatisfied segment was replaced with 0.50. Row 10 in Table 12 displays the Limited Adjusted Response Segment values for each of the segments. These are the Assigned Segment values from row 6 of Table 12 that have been adjusted to reflect the actual percent of customers cancelling in row 3.

The systems and methods of the invention adjust the Mavin Score based on the Adjusted Response Segment Values as shown in row 7 of Table 12. The adjusted total N in row 9 is determined by multiplying the number of responses N for each segment by that segment's Adjusted Response Segment Value and adding those products. As shown in Table 12, the Adjusted Mavin Score is determined by the adjusted total N in row 9 (3,987) divided by the total number of surveys (1000) which equals 3.99. Row 9 displays the Adjusted Mavin Score which used the Adjusted Response Segment Values. As shown in Table 12, the adjusted response segment values can be greater or smaller than the (nominal) Assigned Segment values and lead to adjusted Mavin Scores that may be greater or smaller than the nominal (standard) Mavin Score. When the adjustments are substantial, it supports the additional effort to collect the evidence and information needed to implement the adjustment process, otherwise the simplicity of the assigned values suggest that it be used.

As outlined above, another feature of the Mavin invention is the ability to interpret values above the defensible standard score of 4.00. When Mavin Scores are above 4.00, the two digits to the right of the decimal point (fractional part) can be interpreted as the percent of respondents who are Very Satisfied. This can be clearly demonstrated when all respondents select Satisfied or Very Satisfied. In one exemplary embodiment of the invention, there are 100 respondents and 25 selected Very Satisfied and 75 selected Satisfied. The resultant Mavin Score is 4.25. That is, the two digits to the right of the decimal point (fractional part) are 25, and 25% of the respondents chose Very Satisfied. These two digits (fractional part) always equal the percent Very Satisfied when all respondents chose only Satisfied or Very Satisfied. When responses other than Very Satisfied or Satisfied are included, the same equivalencies apply. The two digits to the right of the decimal point (fractional part) remain interpretable as the percent who are Very Satisfied, but the nomenclature is changed to the "Weighted Percent" Very Satisfied. This is illustrated below in Table 13 where 100 respondents' satisfaction levels were measured: 30 Very Satisfied, 60 Satisfied, 7 Neutral, 2 Dissatisfied, and 1 Very Dissatisfied, and the Mavin Score is 4.16. The "Weighted Percent Very Satisfied" is equivalent to 16.

TABLE 13

| | Demonstration of Weighted Percent Very Satisfied | | | | | | |
|---|---|---|---|---|---|---|---|
| | Very Satisfied | Satisfied | Neutral | Dissatisfied | Very Dissatisfied | Row Totals | Mavin Score |
| Segment Value | 5.00 | 4.00 | 3.00 | 2.00 | 1.00 | — | — |
| N (number of respondents with this segment value) | 30 | 60 | 7 | 2 | 1 | 100 | — |
| N x Value | 150 | 240 | 21 | 4 | 1 | 416 | 4.16 |

Mavin Scores below 4.00 are deemed to be equivalent to having zero respondents who are Very Satisfied, even when there are some respondents who actually chose that answer. This is the logical interpretation of the Mavin Score because the Weighted Satisfied Score is below 4.00. However, a similar interpretive approach can be used. For values from 3.01 to 3.99, the two numbers to the right of the decimal point (fractional part) represent the Weighted Percent Satisfied. Similarly, Mavin Scores of 2.01 to 2.99 represent the Weighted Percent Neutral. Mavin Scores of 1.01 to 1.99 represent the Weighted Percent Dissatisfied. There cannot be Mavin Scores below 1.00, because this score can only occur when all respondents choose Very Dissatisfied.

The systems and methods of the Mavin invention incorporate a purpose-built database and reporting system. For example, when all responses are in Five-Option Likert scales format, the analyses and reporting can include results from any equivalent Five-Option Likert scale. For example, satisfaction, importance, confidence, agreement scores, and other Likert scales can be directly compared.

When combined with this 4.00 standard, the systems and methods of the Mavin invention can compare results across diverse environments and cultures. Because of the interval selection and analysis techniques performed by the Mavin systems, the unique characteristic that the two numbers to the right of the decimal point (fractional part) are equal to the Weighted Percent Very Satisfied for values above 4.00, and the Weighted Scores below 4.00 indicate the degree of need for improvement.

Referring again to the two restaurant managers competing for a promotion to regional manager, those making the decision can look at the overall customer satisfaction for the two restaurants. The Mavin Score allows them to make a clear inference as to which manager has the higher rating and how much higher that rating is in terms of the weighted Mavin Scores. If the difference is one or two percent, the results might be considered too small to impact the decision of whom to promote. But if one of the restaurants displayed a 10% higher Satisfaction score, this difference can well be the deciding factor in whom to promote. Traditional analyses do not support this type of informed judgment. As noted above, one restaurant might have a score of 91 Percent Satisfied, but in truth be inferior to another restaurant with 89 Percent Satisfied.

Example Reporting Operations

Figures 4A, 4B:
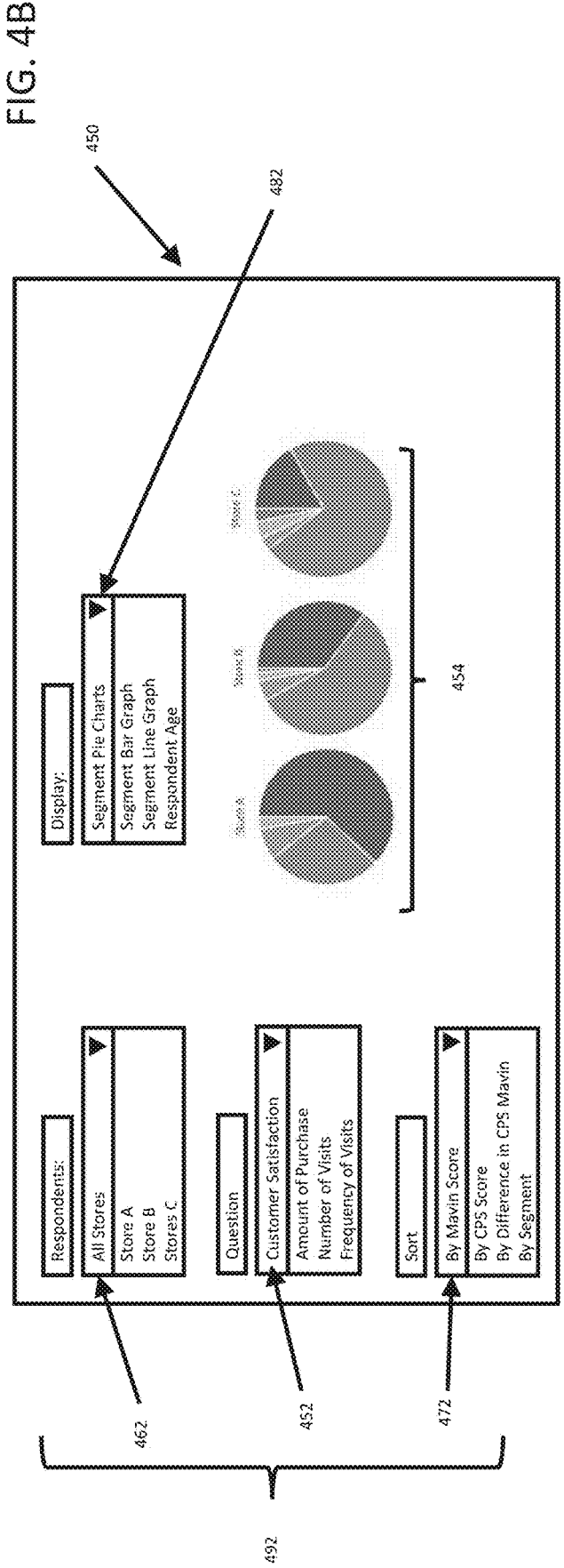
FIGS. 4A and 4B are exemplary display screens generated by a reporting application in accordance with the invention showing options available for presenting and comparing psychometric study results.

FIGS. 4A and 4B are displays 400, 450 of survey responses according to an embodiment of the invention. FIG. 4A shows a table of responses of a survey of customer satisfaction with three automotive parts stores. (See Table 7 also.) The displayed table 400 includes the Five-Option Likert scale results described above. At the top of the table, a first question 402 refers to a survey item and/or a survey segment. The results of the survey responses can be any item that forms a basis for grouping responses. For example, a response grouping can be all the responses to a given survey item (e.g., question), or all the responses from a given segment (e.g., Satisfied), or a combination of survey items and segments. As shown in FIGS. 4A and 4B, the response groupings 404, 454 comprise survey items 402, 452 and survey segments 408, 458. The response grouping 404, 454 can be further parsed for analysis using the display 450 to select response groupings. In the simplified example display 450, a user selected respondents 462 that provided survey results for store A or store B or store C. The user selected the question (survey item) regarding customer satisfaction 452 with the three automotive parts stores. The user indicated that they would like to sort or order the results based on the Mavin Score and display the results 454 as a segment pie chart 482. The results 454 are ordered from left to right by Mavin Score. Selecting different respondents or survey items (questions) or manner of sorting or manner of displaying generates different results. In some examples of the invention, the results can be scaled based on their sorting order or other factors. For example, the pie chart of the store ranking highest by Mavin Score (Store A) can be shown in a relatively larger image than the store ranking lowest by Mavin Score. Depending upon the type of display selected, image sizing or other visual indicators can be altered accordingly.

When survey results are compiled over time, the displays 400, 450 can be changed to illustrate the survey results over a timeline. In addition to comparisons between respondents, stores, questions, and other survey results, the same results can be displayed side by side or overlaid to provide a visual comparison between the survey results over time. Similarly, multiple respondents can be selected so that comparisons between survey results (e.g., Store A versus Store B) can be compared over time.

For each response grouping, the display can include multiple corresponding images and related scores for different times when survey responses were received. These timeline comparisons and displays provide insights into trends, including improvements, declines, and the relative changes between two like sets of results.

The displays also include trend indicators that show result groupings such as dispersion and congregation of response results. That is, over time, the results may show that the difference in survey results for one particular segment or segments compared to another segment or segments is now greater than previously measured. Conversely, the results may show that the difference in survey results for one particular segment or segments is now closer to the results of another segment or segments. The dispersion or congregation of survey results can be displayed in the display 450.

Dispersion (e.g., a wide distribution of scores) and congregation (e.g., a closer grouping of scores) can be determined by establishing a range of scores for each combined segment responding to each survey item using previous scores, target scores, and other benchmark data. The responses can then be mapped or graphed against the target scores. If the responses match or are grouped about the benchmark results, an indication of congregation can be determined and displayed using a number of different techniques, including least squares methods or other regression analysis techniques.

The example displays in FIGS. 4A and 4B can be a user interface 400, 450 that enables a user to select the manner in which the survey responses are displayed. For example, in the example embodiment shown in FIGS. 4A and 4B, the user interface 400, 450 a display control interface 492 allows the user to control how the response groupings 404, 454 are displayed. In this example, display control interface 492 provides drop-down menus that establish which response groupings will be displayed and in what manner. In other example embodiments, other graphical user interface items can be used for selecting user options for the manner in which the response groupings will be displayed. For example, pop up messages can be used as well as a series of windows providing the user questions regarding the desired features of the display.

The user interface 400, 450 provides flexibility and customization for users to view and deliver response groupings on the display. In this example implementation, drop down menus 462, 452, 472, 482 of the display control interface 492 provides options for the user to several variables from which to display and report the response groupings. Each of these variables (options) provides a different basis for determining the characteristics and insights of the survey responses. In some instances, users will want to segment the results by individual store. In other instances, different questions may be selected, displayed, and analyzed to glean insights into the operation of the store(s). In other cases, users will select identify and evaluate satisfaction levels of the quality of the salad bars or the size of the tacos. The user interface 400, 450 provides the flexibility and customization to enable users to identify top performers for recognition and lower performers for remediation. The drop-down menus 462, 452, 472, 482 of the display control interface 492 provide an intuitive and flexible manner for users to identify and recognize performance, quality, and satisfaction levels.

As outlined above, the respondent (segment) drop-down menu 462 provides options for the user to select the segments that the user views. In this example, the "All Stores" option is selected, and all segments and items can be shown on the display. Other options that can be provided by the respondent drop down menu 462 include any type of segment, such as a store, a location, a parts stocking level, and other segments.

The user interface 400, 450 includes a question drop-down menu 452 that allows the user to select whether to view results from a single survey item, a subset of all survey items, or the entire set of survey items. In the example shown in FIGS. 4A and 4B, the question menu shows the "Customer Satisfaction" question selected. A sorting drop-down menu 472 allows the user to select how the results will be ordered and displayed. Grouping types can be combined in some displays (e.g., a line graph) or multiple, single-result displays can be selected. In the example shown in FIGS. 4A and 4B, the sort menu shows that the user has chosen to have the results ordered by "Mavin Score."

The user interface 400, 450 also includes a display drop down menu 482 that provides options for the user to select the manner in which scores are displayed. As outlined above, the user chose to sort/order the results by Mavin Score, and has chosen to display the results as segment pie charts. The results (i.e., response groupings) 454 are shown as pie charts by Mavin Score. That is, Store A's results of the customer satisfaction question, with a Mavin Score of 4.46, is displayed as a pie chart first, Store B's results of the customer satisfaction question, with a Mavin Score of 4.23 is displayed as a pie chart next, and Store C's results of the customer satisfaction question, with a Mavin Score of 3.97 is displayed last. Note that the displayed items would be ordered differently (and in different formats) if the user had chosen to sort the scores with different criteria.

Figure 5:
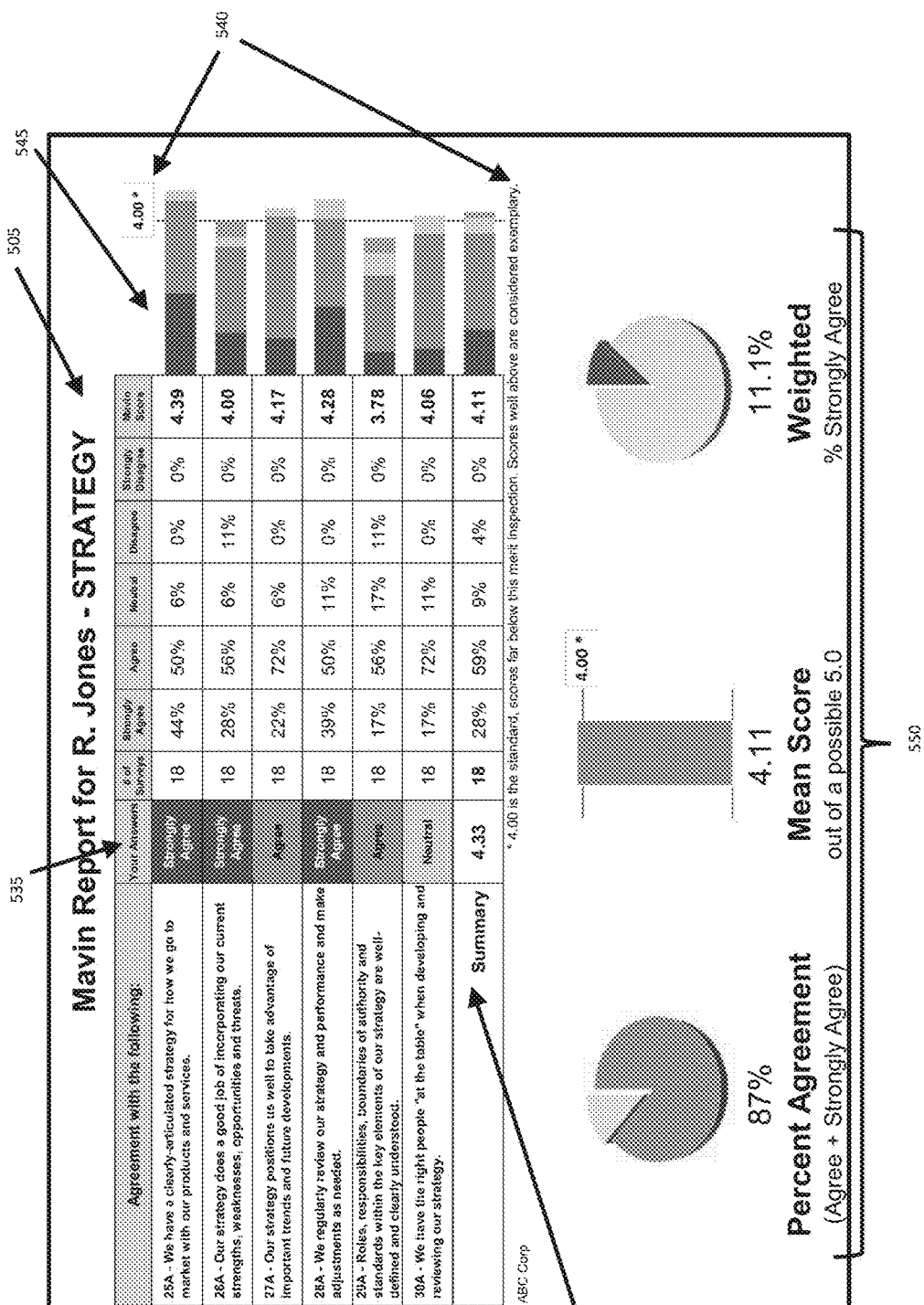
FIG. 5 shows an exemplary display screen generated by a reporting application in accordance with the invention showing data visualization of a survey analyzed using systems and methods of the invention.

FIG. 5 shows an exemplary embodiment of a user interface 500 in accordance with the invention generated by the reporting application. The Mavin Report 505 for R. Jones demonstrates how the systems and methods of the Mavin invention are able to support complex decisions. The Mavin Report 505 shows six Five-Option Likert scale questions 25A, 26A, 27A, 28A, 29A, 30A. "Your Answer" column 535 shows how R. Jones responded to each question 25A, 26A, 27A, 28A, 29A, 30A. "Summary" row 530 provides an indication of how R. Jones responded compared the 18 members of the group that responded. R. Jones' answers 535 are for the most part, in line with the group, with the one exception of item 30A. In addition, the group is up to speed on five of the six items (questions), with item 29A the only one below the standard. That is, 4.00 is the defensible standard score (noted by reference numeral 540) and equating to the "Satisfactory" segment, and on five of the six questions, the Mavin Score was greater than or equal to 4.00. On question 29A, the Mavin Score was 3.78 (i.e., less than the defensible standard, which identifies an area for improvement. The data are displayed in tabular form 545 plus graphic form (reference numeral 545 is a bar graph and reference numeral 550 are charts). The table and the graphics provide a clear and intuitive visualization of the Mavin Scores and the defensible standard (4.00), clearly differentiating the degree to which the group met this goal.

In exemplary embodiments, the reporting application provides real-time customizable graphical user interfaces to the display devices of the user and displays the psychometric study results by segments in the fully anchored scale as well as display the determined Mavin Score of the psychometric study results. The reporting application can be customized by the user to display an ordered set of psychometric study results based on the Mavin Score. Comparisons can be made using the reporting application that include comparisons of respondents, entities, survey responses, and other variables (additional responses, for example). The comparisons can be customized and displayed as charts, graphs, infographics, diagrams, maps, and other data visualization presentations.

The on-the-fly customizable reporting application communicates the psychometric study results clearly and effectively to users. The data visualization techniques performed by the reporting application visually communicates the study results so users can interpret and understand the results. The data visualization methods in accordance with the invention provide a visual storytelling of the survey results to make apparent trends and outliers within the study results, tell a story found within the data, reinforce or contradict opinions, and highlight those study results that most accurately support the goals of the organization.

The systems and methods in accordance with the invention overcome deficiencies of prior systems in analyzing, ordering, and displaying survey responses, including problems identified with combined percentages satisfied measures and other data skewing that occurs when analyzing Likert-type scale response data. The systems and methods of the invention more appropriately weight respondent passion and outliers, which leads to better organizational decision making. The technological improvements solve the above problems and improve the functioning of survey systems by aiding evaluators in identifying the most noteworthy results of a survey. These insights allow an organization or other evaluator to quickly and accurately identify areas with a need for impactful change or prominent recognition. This allows the organization or other evaluator to focus its scarce resources on those areas.

The systems and methods in accordance with the (Mavin) invention provide computerized evaluation systems for analyzing aggregate survey research data and providing actionable intelligence based on the analysis. The Mavin invention overcomes problems of prior systems in reviewing, analyzing, communicating, and displaying respondent impressions from survey data and psychometric study results. The systems and methods of the invention identify, categorize, and classify study results and transfer these qualities into quantitative measures for data analysis and visualization purposes.

I claim:

1. A computerized evaluation system for storing, scoring, and reporting results from a psychometric study of an entity, the system comprising:
   a processor to execute applications stored in a non-transitory computer-readable medium, the applications comprising:
   a scoring application that determines a Mavin Score of the stored study results, wherein the Mavin Score determination includes:
   segmenting the study results into a fully anchored scale with a predetermined number of segments;
   weighting each of the predetermined number of segments with an assigned response segment value;
   determining a defensible standard score based on the number of predetermined segments;

extracting interval scoring results from the segmented study results, wherein the extracted interval scoring results include a predetermined interval weighting; and generating a Mavin Score based on the assigned response segment values, the segmented study results of the predetermined number of segments, and the extracted interval scoring results;

automatically comparing the generated Mavin Score and the defensible standard score; and automatically generating a single weighted evaluation metric based on the comparison for evaluation of the performance of an entity.

2. A computerized evaluation system of claim 1, wherein the predetermined interval weighting is an adjusted response segment value determined by:

a) comparing evidence-based results corresponding to each of the predetermined segments;

b) determining a relative change in the evidence-based results between two or more of the predetermined segments based on the comparison of step a);

c) normalizing the relative change in the evidence-based results of step b) based upon a relative change of the evidence-based results for the segment corresponding to the defensible standard score;

d) determining an adjusted response segment value for one of the predetermined segments based upon the normalized relative change of step c), the assigned response segment value corresponding to the predetermined segment, and a next higher assigned response segment value for a second predetermined segment; and wherein the Mavin Score is an adjusted Mavin Score generated based on the adjusted response segment values, the segmented study results of the predetermined number of segments, and the predetermined interval weighting.

3. A computerized evaluation system of claim 2, wherein the evidence-based results include results of an action taken by a respondent that provided a response to the psychometric study.

4. A computerized evaluation system of claim 2, wherein the adjusted Mavin Score is further based on a number of responses for each of the segments and the adjusted segment values for each of the segments.

5. A computerized evaluation system of claim 2, wherein the adjusted response segment value for each of the segments is limited to the assigned response segment value ±0.5.

6. A computerized evaluation system of claim 2, wherein automatically comparing the generated Mavin Score includes automatically comparing the generated adjusted Mavin score and the defensible standard score, including:

determining when the adjusted Mavin Score is less than the defensible standard score, and sending a notice of failure to recipients on a distribution list; and determining when the adjusted Mavin Score is greater than or equal to the defensible standard score, and sending a positive notice of evaluation to recipients on a distribution list.

7. A computerized evaluation system of claim 2, wherein the adjusted Mavin Score is greater than the defensible standard score, and wherein the single weighted evaluation metric is represented in decimal notation, and includes an integral part and a fractional part, and wherein the integral part denotes the segment of the fully anchored scale indicative of the respondents' general characterization of the psychometric study results.

8. A computerized evaluation system of claim 7, wherein the fully anchored scale is a Likert scale, and wherein the predetermined number of segments is five, and I. when the integral part of the single weighted evaluation metric has a segment value of "4," then the respondents' general characterization of the psychometric study results is classified as Very Satisfied and then the fractional part of the single weighted evaluation metric designates the weighted percent of Very Satisfied respondents; and II. when the integral part of the single weighted evaluation metric has a segment value of "3," then the respondents' general characterization of the psychometric study results is classified as Satisfied and then the fractional part of the single weighted evaluation metric designates the weighted percent of Satisfied respondents; and III. when the integral part of the single weighted evaluation metric has a segment value of "2," then the respondents' general characterization of the psychometric study results is classified as Neutral and then the fractional part of the single weighted evaluation metric designates the weighted percent of Neutral respondents; and IV. when the integral part of the single weighted evaluation metric has a segment value of "1," then the respondents' general characterization of the psychometric study results is classified as Dissatisfied and the fractional part of the single weighted evaluation metric is not zero, then the non-zero fractional part of the single weighted evaluation metric designates the weighted percent of Dissatisfied respondents, and when the fractional part of the single weighted evaluation metric is zero, then the zero fractional part of the single weighted evaluation metric designates the weighted percent of Very Dissatisfied respondents.

9. A computerized evaluation system of claim 2 further comprising:

a reporting application to provide a real-time customizable graphical user interface to the display device of the user and display the study results by segments in the fully anchored scale, display the determined adjusted Mavin Score of the study results, and display an ordered set of study results based on the adjusted Mavin Score.

10. A computerized evaluation system of claim 1, wherein the predetermined interval weighting is greater than 1.0 for one or more of the predetermined segments with an assigned response segment value lower than a mean of interval scoring results.

11. A computerized evaluation system of claim 1, wherein the predetermined interval weighting is less than 1.0 for one or more of the predetermined segments with an assigned response segment value lower than a mean of interval scoring results.

12. A computerized evaluation system of claim 1, wherein the psychometric study is a questionnaire.

13. A computerized evaluation system of claim 1, wherein the psychometric study results are responses scaled using one of the group of a satisfaction scale, an importance scale, a confidence scale, and an agreement scale.

14. A computerized evaluation system of claim 1, wherein the psychometric study results are responses scaled using a Likert scale.

15. A computerized evaluation system of claim 1, wherein the fully anchored scale is a Likert scale.

16. A computerized evaluation system of claim 1, wherein the predetermined number of segments is five or seven.

17. A computerized evaluation system of claim 1, wherein extracting interval scoring data includes extracting interval scoring data using non-linear intervals.

18. A computerized evaluation system of claim 1, wherein the single weighted evaluation metric generated by the reporting application is compared to a single weighted evaluation metric of a different entity as a comparison of relative performances of the entities.

19. A computerized evaluation system of claim 1, wherein the single weighted evaluation metric is compared to an additional evaluation metric for the entity to track relative performance of the entity over time.

20. A computerized evaluation system of claim 1, wherein the single weighted evaluation metric generated by the reporting application is compared to a series of additional single weighted evaluation metrics for the entity to determine the degree to which an entity's performance increases or decreases over time.

* * * * *